(12) United States Patent
Schmidt et al.

(10) Patent No.: US 7,754,877 B2
(45) Date of Patent: Jul. 13, 2010

(54) METHOD FOR PRODUCING REACTIVE CYCLODEXTRINS, TEXTILE MATERIAL PROVIDED WITH SAME, AND USE OF SAID CYCLODEXTRIN DERIVATIVES

(75) Inventors: Andreas Schmidt, Langenfeld (DE); Hans-Jürgen Buschmann, Kempen (DE); Dierk Knittel, Krefeld (DE); Eckhard Schollmeyer, Rheurdt (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 1078 days.

(21) Appl. No.: 10/495,517

(22) PCT Filed: Nov. 14, 2002

(86) PCT No.: PCT/EP02/12716

§ 371 (c)(1),
(2), (4) Date: Nov. 2, 2004

(87) PCT Pub. No.: WO03/042449

PCT Pub. Date: May 22, 2003

(65) Prior Publication Data

US 2005/0080254 A1    Apr. 14, 2005

(30) Foreign Application Priority Data

Nov. 14, 2001  (DE) ................. 101 55 781

(51) Int. Cl.
*C08B 37/16* (2006.01)
(52) U.S. Cl. .................... 536/124; 536/103
(58) Field of Classification Search ........... 536/124, 536/103; *C08B 37/16*
See application file for complete search history.

(56) References Cited

U.S. PATENT DOCUMENTS

| 4,064,118 | A | * | 12/1977 | Wong ............... 530/385 |
| 5,319,078 | A | | 6/1994 | Ikenaka et al. ........ 536/18.7 |
| 5,357,012 | A | * | 10/1994 | Nussstein et al. ...... 526/238.2 |
| 5,385,981 | A | * | 1/1995 | Kruger et al. ........ 525/276 |
| 5,391,718 | A | * | 2/1995 | Tzikas et al. ......... 534/637 |
| 5,594,125 | A | | 1/1997 | Seyschab et al. ...... 536/103 |
| 5,654,422 | A | | 8/1997 | Hirsenkorn .......... 536/103 |
| 5,728,823 | A | | 3/1998 | Reuscher et al. ...... 536/46 |
| 5,776,842 | A | * | 7/1998 | Wood et al. .......... 442/394 |
| 5,929,131 | A | * | 7/1999 | Bowen ............... 523/116 |
| 2004/0129640 | A9 | * | 7/2004 | Ng et al. ............. 210/656 |

FOREIGN PATENT DOCUMENTS

| DE | 40 35 378 | 5/1992 |
| DE | 44 29 229 | 2/1996 |

OTHER PUBLICATIONS

Goebel, W.F. and Avery, O.T., "Chemo-Immunological Studies on Conjugated Carbohydrate-Proteins", 1931, Journal of Experimental Medicine, 54, p. 431-436.*
Himmelspach, K. and Wrede, J., "Use of 2-[(aminophenyl)-sulfonyl]-ethyl Hydrogen Sulfate for the Preparation of a Dextran-specific Immunogen", 1971, FEBS Letters, 18, p. 118-120.*
Kuznetsov, P. V. "Up-To-Date State of the Synthesis of AZO Adsorbents of the Affinity Type for the Investigation of Physiologically Active Substances (Review)", Pharmaceutical Chemistry Journal, 1993, 27(12), p. 857-867.*
Definition of a circular definition, Dictionary.com, http://dictionary.reference.com, accessed online on Sep. 11, 2008.*
Bravo-Diaz et al. Langmuir, 2005, 21, p. 4888-4895.*
Bravo-Diaz et al. Langmuir, 1999, 15, p. 2823-2828.*
A. Ueno et al., Macromol. Rapid Commun. vol. 19, pp. 315-317 (1998).
N. Rogmann et al., Carbohydrate Research 327 (2000) pp. 269-274.
Derwent Abst. No. 92-167903/21 of DE 40 35 378.

* cited by examiner

*Primary Examiner*—Shaojia Anna Jiang
*Assistant Examiner*—Jonathan S Lau
(74) *Attorney, Agent, or Firm*—Shiela A. Loggins

(57) ABSTRACT

The invention relates to a process for the preparation of reactive cyclodextrins, in which process the cyclodextrins CD are reacted with a bifunctional alkyl compound X—$(CH_2)_n$—Y, wherein X is a group which reacts with CD, n is an integer from 2 to 20 and Y is a group which reacts with a group Z or is a group-Reactive which is capable of reaction with cellulosic or proteinic materials and, optionally, in a further step, insofar as Y is a group which reacts with a group Z, the resulting product is reacted with a reactive anchor compound Z-Reactive to form the reactive cyclodextrin, and also to reactive cyclodextrins prepared in accordance therewith, to materials dressed therewith and to the use thereof.

13 Claims, No Drawings

METHOD FOR PRODUCING REACTIVE CYCLODEXTRINS, TEXTILE MATERIAL PROVIDED WITH SAME, AND USE OF SAID CYCLODEXTRIN DERIVATIVES

This application is the national stage entry of PCT/EP02/12716, filed Nov. 14, 2002.

BACKGROUND

The present invention relates to a process for the preparation of reactive cyclodextrins, cyclodextrin derivatives or mixtures thereof, to a textile material dressed therewith, and to the use thereof.

Cyclodextrins are to be understood generally as being cycloamyloses and cycloglucans which are formed as cyclic dextrins by the action of cyclodextrin glycosyltransferase in the degradation of starch by Bacillus macerans and/or Bacillus circulans. They consist of 6, 7 or 8 glucose units $\alpha$-1,4-linked to form a cyclic structure, thereby defining the $\alpha$-, $\beta$- and $\gamma$-cyclodextrins, respectively, and are compounds of a kind which may be represented by formula I

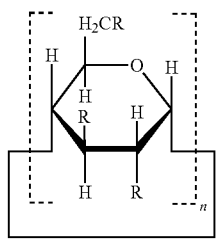

Formula I

The cyclodextrins have a ring size wherein n is 5, 6, 7 or 8. The substituent R is defined as an OH group.

Cyclodextrins are bound into a crystal lattice and are so layered on top of one another that they form continuous intramolecular channels in which hydrophobic guest molecules, e.g. gases, alcohols or hydrocarbons, may be included in varying amounts up to saturation. That process is referred to as "molecular encapsulation" ("molekulare Verkapselung", Römpp "Chemie Lexikon", Vol. 2, 1995, 9th expanded edition). By virtue of that property, cyclodextrins are used in the production of foods, cosmetics, pharmaceuticals and pesticides and also in solid-phase extraction.

A large number of reactive cyclodextrin derivatives and processes for their preparation are already known. EP-A-0 483 380 discloses a process in which the bonding of cyclodextrins (the abbreviation CD will be used in formulae herein below) to polymers by way of an acetal bond is described. In the preparation of those cyclodextrin derivatives, aldehyde groups in protected or unprotected form are introduced into the cyclodextrin compounds. These compounds then react with the nucleophilic hydroxyl groups of a polymer. The disadvantage of that bonding is the low stability of acetals in respect of acidic conditions.

It is also known for $\beta$-cyclodextrin to be reacted under aqueous conditions with epichlorohydrin under Lewis acid conditions. The article by A. Deratani and B. Pöpping in Makromol. Chem., Rapid Commun. 13, 237-41 (1992) describes that $\beta$-cyclodextrin can be reacted under aqueous conditions with epichlorohydrin under Lewis acid conditions using $Zn(BF_4)_2$ as catalyst to form a cyclodextrin-chlorohydrin (3-chloro-2-hydroxypropyl-cyclodextrin derivative). That derivative is capable of reacting under basic conditions with nucleophiles such as, for example, $OH^-$ ions. The disadvantage of that reaction is that, under the Lewis acid conditions, it is possible to achieve only a very low degree of incorporation of epichlorohydrin. For that reason, a large excess of epichlorohydrin is employed. However, those large amounts give rise to toxic or carcinogenic subsidiary products, which have to be separated off and destroyed.

DE-A-44 29 229 discloses the preparation and use of cyclodextrin derivatives containing at least one nitrogen-containing heterocycle having at least one electrophilic centre. The nitrogen-containing heterocycles are usually tirazines and quinoxalines which are used as reactive anchors for bonding to, for example, membranes, foils, films, textiles, leather, chromatographic separation phases etc. In the case of those materials dressed with $\beta$-cyclodextrin, the cavities in not all the fixed cyclodextrins are accessible.

Such reactive anchors are well known from textile dyeing. In the case of that process too, subsidiary products—so-called hydrolysates—are formed in the course of the bonding, which cannot be reused and consequently have to be disposed of as waste.

The problem of the present invention is consequently to make available a process which gives rise to only a small amount of harmful or non-reusable subsidiary products and which does not have the otherwise known disadvantages of the prior art, but which is at the same time suitable for the reaction with cellulosic and proteinic materials, especially fibres.

BRIEF DESCRIPTION OF THE INVENTION

The present invention accordingly relates to a process for the preparation of reactive cyclodextrins, in which process the cyclodextrins CD are reacted with a bifunctional alkyl compound X-spacer-Y, wherein X is a group which reacts with CD, the spacer is a hydrocarbon radical containing from 2 to 25 carbon atoms and Y is a group which reacts with a group Z or is a group-Reactive which is capable of reaction with cellulosic or proteinic materials and, optionally, in a further step, insofar as Y is a group which reacts with a group Z, the resulting product is reacted with a reactive anchor compound Z-Reactive to form the reactive cyclodextrin.

In accordance with the invention cyclodextrins are understood to be those containing from 6 to 8 glucose units, and also derivatives, substitution products and mixtures thereof.

The process according to the invention can be carried out in one stage, the direct product being a cyclodextrin provided with a reactive anchor function by way of a spacer group —$(CH_2)_n$—. Alternatively, the process is carried out in two stages, the spacer group provided with a reactive function being introduced in a first step and then, in turn, being reacted with a reactive anchor compound Z-Reactive.

DETAILED DESCRIPTION OF THE INVENTION

The reactive anchor function refers to a chemically active group which is capable of entering into a chemical bond with cellulosic and/or proteinic materials and consequently of chemically bonding the cyclodextrin by way of the spacer group. Such reactive anchor functions are known to the person skilled in the art and are used—for other purposes—in the dyeing of textiles with reactive dyes.

Bifunctional alkyl compounds X—$(CH_2)_n$—Y are understood to be those compounds that are provided with two different functions, one of which can react with cyclodextrins, and the other of which can react with a reactive anchor compound or is itself a reactive anchor function which can react chemically with proteinic or cellulosic materials. Examples of such functions are halogens, primary and secondary amine, hydroxyl, mercapto, isocyanato, sulfonyl, carboxyl, diazonium and aryl groups and the like.

As spacer group there are used aliphatic, cycloaliphatic or aromatic hydrocarbon radicals containing from 1 to 25 carbon atoms. Preference is given to straight-chain or branched aliphatic groups containing up to 20 carbon atoms, especially —$(CH_2)_n$—. n is an integer from 1 to 20, preferably from 1 to 8 and especially from 2 to 6. Preference is likewise given to cyclic and aromatic spacers, such as —$(C_6H_{10})$— and —$(C_6H_4)$—, and also to arylalkyl groups, such as —$H_2$—$(C_6H_4)$— or —$(CH_2)_2$—$(C_6H_4)$—.

The functional groups of the bifunctional alkyl compounds are arranged in terminal positions so that they are spaced as far apart from one another as possible. As a result, the said bifunctional alkyl compounds fulfil their function as a spacer group, that is to say an organic compound which creates maximum spacing between the cyclodextrin and the material to which it is intended to adhere. This significantly improves the accessibility of the cyclodextrins for their loading with useful or harmful substances.

Preference is given to the use, as bifunctional alkyl compounds, of haloaminoalkyl compounds (in the form of their salts) or haloalkylaryl compounds, for example 2-chloroethylbenzene, 3-chloropropylbenzene, chloroethylammonium or bromopropylammonium salts. In the latter case the amine function primes the attachment point for the adhesion of the reactive anchor compound, which then makes the cyclodextrin ready for coupling to a cellulosic or proteinic material.

The reactive anchor compounds of the kind used in the invention in the second stage include reactive derivatives of, for example, 2-bromoacrylic acid, 2,3-dibromopropionic acid, 2-chloroacrylic acid, methacrylic acid or acrylic acid, or also vinyl sulfone. As a reactive group those compounds are employed in a precursory stage as acid chlorides or acid bromides. Also suitable are reactive triazine and quinoxaline derivatives, especially halogenated compounds thereof, as are described in DE-A-44 29 229.

When the bifunctional alkyl compounds are haloalkylbenzenes, the coupling of the reactive anchor to the benzene ring is advantageously performed by means of diazotisation with a suitable aromatic diazonium compound which has a further function capable of reacting with the cellulosic or proteinic material. Such functions are, for example, sulfonic acid groups and hydrogen sulfate groups as are known from the textile industry for the reactive dyeing of textiles. An example of a suitable compound is 2-[(p-aminophenyl)sulfonyl]ethyl hydrogen sulfate, which, after conversion into a diazonium salt, can be coupled to a phenyl group or substituted phenyl group of a cyclodextrin functionalised with the bifunctional alkyl compound and then, by way of the hydrogen sulfate function, is reactively bonded to cotton.

The two process variants shall be briefly illustrated below by means of Scheme 1.

Scheme 1:
Synthesis of novel reactive cyclodextrin derivatives

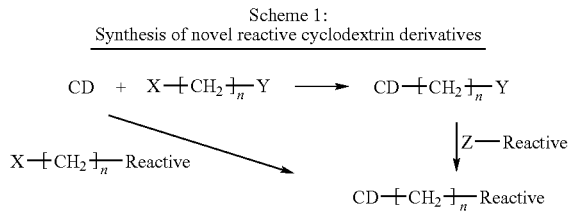

The abbreviation CD in the Scheme shown above denotes the cyclodextrins. In accordance with the first process variant, which proceeds by way of a two-stage process, the cyclodextrin molecule used is first reacted with a bifunctional alkyl compound. As already mentioned, the bifunctional alkyl compound is, for example, one that has halo-amino functions (amino-CD) or halo-aryl functions (aryl-CD). By way of example, a bifunctional alkyl compound having a halo-amino function may be described; as can be seen from FIG. 1, the halogen function of the bifunctional alkyl compound reacts with the free OH groups of the cyclodextrin (the amine function being protected in the form of an ammonium salt in the starting compound).

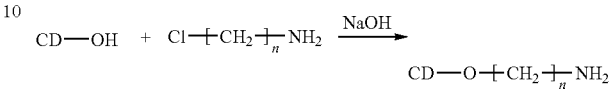

FIG. 1: General reaction mechanism for the synthesis of cyclodextrins having amino functions, wherein n is an integer from 1 to 20.

The reaction is carried out at temperatures from 50° C. to 100° C., preferably at temperatures in the range from 80° C. to 100° C. An alkaline aqueous solution is used as reaction medium.

Besides NaOH, there may be used KOH, LiOH or CsOH. Preference is given to KOH and NaOH.

The reaction is carried out at normal pressure so that, advantageously, pressurised vessels do not have to be used for the reaction procedure, as has hitherto been necessary in the prior art, in order to obtain high yields.

The reaction time is in the range from 1 hour to 12 hours; preference is given to reaction times of from 2 hours to 7 hours.

The ratio of cyclodextrin to the bifunctional alkyl compound used is in the region of up to 1:15, preferably up to 1:8, and especially 1:5, based on the relative molar amounts of starting materials employed. The reaction procedure is so selected that the pH value decreases over the reaction time, and buffer systems, as are known from the prior art, do not have to be used. This ensures an improved reaction procedure without further product losses caused by the removal of auxiliaries. The end of the reaction is reached when the pH value no longer decreases. The solvent is removed in vacuo and the residue is recrystallised.

In accordance with this reaction scheme, it is possible to introduce a spacer of any desired size—that is to say a bifunctional alkyl compound containing any desired number of carbon atoms—between the cyclodextrin and the amino group or aromatic moiety. The amino group and the aromatic ring are consequently available for further reactions.

In a second reaction step, in the process according to the invention, the reactive anchor, or Z-Reactive, is reacted with the purified product of the first stage of the process. As reactive anchor there is used, by way of example, as can be seen from FIG. 2, dibromopropionyl chloride. The reaction is carried out in anhydrous organic solvents at temperatures of from 30° C. to 70° C.

This reaction is also carried out at normal pressure so that, advantageously, pressurised vessels do not need to be used for the reaction procedure, as has hitherto been necessary in the prior art, in order to obtain high yields.

The reaction time is in the range from 1 hour to 12 hours; preference is given to reaction times of from 2 hours to 7 hours.

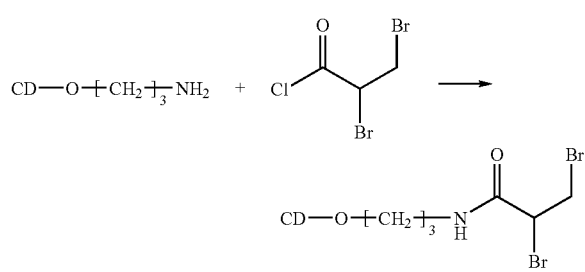

FIG. 2: Reaction for bonding 2,3-dibromopropionyl chloride to an amino-CD product In another embodiment, the cyclodextrin can be coupled to the reactive anchor directly, using a spacer, in a one-stage reaction. The reaction conditions are almost identical to those of the two-stage reaction. In contrast thereto, however, it is possible to use an aqueous solvent in this case.

The invention relates also to reactive cyclodextrins having a reactive anchor function-Reactive which is bonded to a spacer group and is capable of reaction with cellulosic and/or proteinic materials.

The advantage of this system over one comprising D-cyclodextrin bonded, for example, by way of nitrogen-containing heterocycles is the better accessibility of the cavities of all the fixed cyclodextrins.

As spacer group there are used aliphatic, cycloaliphatic or aromatic hydrocarbon radicals containing from 1 to 25 carbon atoms. Preference is given to straight-chain or branched aliphatic groups containing up to 20 carbon atoms, especially —(CH$_2$)$_n$—. n is an integer from 1 to 20, preferably from 1 to 8 and especially from 2 to 6. Preference is likewise given to cyclic and aromatic spacers, such as —(C$_6$H$_{10}$)— and —(C$_6$H$_4$)—, and also arylalkyl groups, such as —CH$_2$—(C$_6$H$_4$)— or —(CH$_2$)$_2$—(C$_6$H$_4$)—.

The reactive anchor functions-Reactive used herein are functions such as 2,3-dibromo-propionyl, 2-bromoacryloyl, 2-chloroacryloyl, methacryloyl, acryloyl or vinyl sulfone groups, sulfonic acid radicals or hydrogen sulfate radicals, and also triazinyl and quinazolinyl groups, especially halogenated derivatives thereof.

The invention relates also to a material dressed with reactive cyclodextrins, wherein the reactive cyclodextrins are bonded by the reactive anchor function, by way of the spacer function, to free OH or NH$_2$ functions of the material.

The dressed material includes materials that consist of natural protein-containing or cellulose-containing or synthetic compounds. The dressed material is especially a textile material.

The term "textile materials" is understood to include fibres, filaments, yarns, spun material, heaped material and sheet material and also barrier films.

The term "cyclodextrins" is understood in the context of the present invention to include α-, β- and γ-cyclodextrin, including mixtures thereof and in the form of their known derivatives insofar as the latter are capable of reaction in accordance with the invention.

The term "cyclodextrin derivatives" is understood in the context of the invention also to include, especially, partially methylated, ethylated, substituted or unsubstituted cyclodextrins or mixtures thereof.

In the context of the invention, the term "substituted cyclodextrin derivatives" means that the cyclodextrin may be substituted one or more times by $C_{1-14}$alkyl, $C_{2-14}$alkenyl, OH, carbonyl, carboxyl or amine groups.

Textile material is understood to include both natural and synthetic or synthetic-fibre-containing materials. Natural textile materials are understood to include cotton, wool, linen and silk. Cellulose-based textile fibres are cotton, linen, rayon staple or artificial silk. These also include viscose, cupro and acetate. The term "synthetic fibres" is understood to include fully synthetic fibres produced from simple building blocks by polymerisation, polycondensation or polyaddition. These include elastane, elastodiene, fluorofibres, polyacrylic, modacrylic, polyamide, aramid, polyvinyl chloride, polyvinylidene chloride, polyester, polyethylene, polypropylene and polyvinyl alcohol. Synthetic-fibre-containing materials are those that comprise both entirely synthetic fibres and also natural materials such as those based on cellulose.

The reactive cyclodextrins prepared by the process according to the invention are covalently bonded to the matrix of the material by the reactive anchor.

The present invention relates also to the use of the materials dressed with the reactive cyclodextrins in accordance with the process in taking up and delivering pharmaceutically active substances. As a result of the fact that all the cyclodextrins or derivatives bonded by way of the spacers can be utilised completely, they are advantageously capable of the incorporation and controlled delivery of a relatively large amount of active substances. In addition, by virtue of the incorporation in cyclodextrin and the binding behaviour thereof, it is often/in some cases possible to dispense with auxiliaries in the formulation. As active substances there may be mentioned here, by way of example, pharmaceutical active ingredients, herbicides, fungicides, insecticides, biocides, fragrances, perfumes, flavourings, stabilisers, dyes or the like.

In addition, the dressed materials can be used for the incorporation of harmful substances from the air or as filters and for the incorporation of hydrophobic or partly hydrophobic substances from an aqueous phase in waste water purification and in water purification.

The reactive cyclodextrins can furthermore be used for the purpose of converting compounds such as insoluble polymers or biopolymers which carry nucleophilic groups, especially free hydroxy groups, into modified polymers so that they have the property of solubilising substances that are of low solubility in water. As polymers there may be mentioned here, by way of example, cellulose, cellulose derivatives, gelatin, chitin, polyalkylamines or polyvinyl alcohols.

An additional application consists in the inclusion of compounds which can, in that way, be stabilised and released in controlled manner. Furthermore, the materials dressed with the reactive cyclodextrins can absorb selective substances.

EXAMPLES

The Examples that follow are intended to illustrate the present invention in greater detail without, however, limiting it in any way.

Example 1

Synthesis of Starting Substances, Cyclodextrins Having Amino Functions (Amino-CD) or Aromatic Moieties (Ar-CD)

a. Derivatisation of Cyclodextrin with 1-chloro-3-aminopropane 2.06 g (0.022 mol) of 1-chloro-3-aminopropane (in hydrochloride form), 5.00 g (0.0044 mol) of β-cyclodextrin and 0.88 g (0.022 mol) of NaOH were dissolved in 250 ml of distilled water and refluxed at 100° C. for 6 hours. After the reaction was complete, the pH was still slightly alkaline. The water was then removed to dryness. For the purpose of purification, recrystallisation was carried out using a small amount of distilled water. A white crystalline powder (amino-CD(a)) was obtained.

b. Derivatisation of Cyclodextrin with 1-bromo-4-aminobutane 3.35 g (0.022 mol) of 1-bromo-4-aminobutane (in hydrochloride form), 5.00 g (0.0044 mol) of β-cyclodextrin and 0.88 g (0.022 mol) of NaOH were dissolved in 250 ml of distilled water and refluxed at 100° C. for 6 hours. After the reaction was complete, the pH was still slightly alkaline. The water was then removed to dryness. For the purpose of purification, recrystallisation was carried out using a small amount of distilled water. A white crystalline powder was obtained.

c. Derivatisation of Cyclodextrin with 1-chloro-2-phenylethane 3.09 g (0.022 mol) of 1-chloro-2-phenylethane, 5.00 g (0.0044 mol) of β-cyclodextrin and 0.88 g (0.022 mol) of NaOH were dissolved in a mixture of 100 ml of acetone and 100 ml of distilled water and refluxed at 90° C. for 6 hours. After the reaction was complete, the pH was still just slightly alkaline. The solvent mixture was then removed to dryness. For the purpose of purification, recrystallisation was carried out using a small amount of distilled water. A white crystalline powder was obtained.

Bonding was then carried out by the customary practice of dyeing using precisely those reactive anchors.

Example 2

Further Processing of Amino-CD

Linkage to a Reactive Anchor 1. 2,3-Dibromopropionyl chloride 5.00 g (0.0035 mol) of amino-CD from Example 1.a were slurried with 4.41 g (0.018 mol) of 2,3-dibromopropionyl chloride in 250 ml of anhydrous dioxane and treated at 50° C. for 5 hours. After the treatment period, the solvent was removed in vacuo. A white crystalline powder (1) was obtained, see FIG. 2.

FIG. 2: Reaction for Bonding 2,3-dibromopropionyl chloride to amino-CD(a)

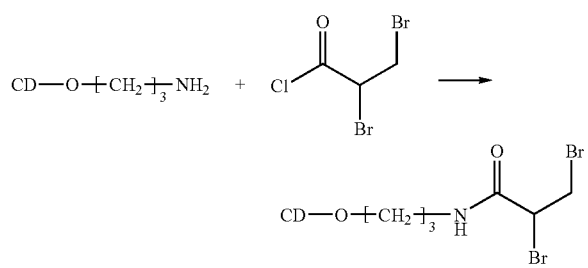

Product: 1

Using the powder obtained, cyclodextrin was covalently bonded to cellulosic and proteinic materials.

2. 2-Methylacrylic acid chloride 5.00 g (0.0035 mol) of amino-CD(a) were slurried with 1.84 g (0.018 mol) of 2-methylacrylic acid chloride in 250 ml of dry dioxane and treated at 50° C. for 5 hours. After the treatment period, the solvent was removed in vacuo. A white crystalline powder (2) was obtained.

Example 3

Using the powder obtained, cyclodextrin was covalently bonded to cellulosic and proteinic materials.

It was possible for the reactive CD derivatives produced in that manner to be applied to textile support materials (e.g. cotton, wool) by simple means analogously to customary dyeing techniques for reactive dyes. The cotton and ECE wool used was purchased from Testex Prüftextilien (Windheckenweg 53, D-53902 Bad Münstereifel/Germany).

1. Linkage with Product 1

5 g of cotton were immersed in a solution of 10 g of 1 from Example 2.1 in 100 ml of demineralised water. The pH of the solution was adjusted to 10.0 using 1.0 mol/l NaOH solution. After being completely wetted, the fabric was padded (liquor take-up 80%), dried in a Matthis dryer at 80° C. for 10 minutes and fixed at 160° C. for 7 minutes. The fabric was then thoroughly rinsed once using hot water and three times using cold water. Detection of the covalently bonded cyclodextrins on the cotton was carried out by measuring the colour discharged from an alkaline phenolphthalein solution.

Cyclodextrin decolourised alkaline phenolphthalein solution (J. Chem. Soc. Perkin Trans. 2, 1992). It was accordingly possible to determine the fixing of cyclodextrin by means of the decolourisation of an alkaline phenolphthalein solution.

2. Linkage with Product 2

5 g of ECE wool were immersed in a solution of 10 g of 2 from Example 2.2 in 100 ml of demineralised water. The pH of the solution was adjusted to 10.0 using 1.0 mol/l NaOH solution. After being completely wetted, the fabric was padded (liquor take-up 80%), dried in a Matthis dryer at 80° C. for 10 minutes and fixed at 160° C. for 7 minutes. The fabric was then thoroughly rinsed once using hot water and three times using cold water. Detection of the covalently bonded cyclodextrins on the wool was carried out by measuring the colour discharged from an alkaline phenolphthalein solution.

Example 4

Further Processing of Ar-CD 5.06 g (0.018 mol) of 2-[(p-aminophenyl)sulfonyl]ethyl hydrogen sulfate were dissolved in 54 ml of 1 molar hydrochloric acid (0.054 mol) with cooling (T<5° C.). Whilst stirring vigorously and cooling, 1.24 g (0.018 mol) of sodium nitrite were added, the temperature not being allowed to exceed 5° C. Towards the end of the addition of the nitrite, testing for free nitrous acid was carried out using iodine starch paper. Nitrous acid was added for as long as the test still gave a positive result 5 minutes after the addition. Excess nitrous acid was destroyed with a small amount of urea.

Then 5.00 g (0.0035 mol) of Ar-CD from Example 1.c were added also at 0-5° C. The solution was neutralised with sodium carbonate and the product was salted out using finely ground sodium chloride. The product was filtered off and recrystallised from a small amount of water. A pale yellow crystalline powder (3) was obtained.

Example 5

5 g of cotton were immersed in a solution of 10 g of 3 from Example 4 in 100 ml of demineralised water. The pH of the solution was adjusted to 10.0 using 1.0 mol/l NaOH solution. After being completely wetted, the fabric was padded (liquor take-up 80%), dried in a Matthis dryer at 80° C. for 10 minutes and fixed at 160° C. for 7 minutes. The fabric was then thoroughly rinsed once using hot water and three times using cold water. Detection of the covalently bonded cyclodextrins on the cotton was carried out by measuring the colour discharged from an alkaline phenolphthalein solution.

Example 6

Derivatisation of CD with 2-[(p-aminophenyl)sulfonyl]ethyl hydrogen sulfate 5.06 g (0.018 mol) of 2-[(p-aminophenyl)sulfonyl]ethyl hydrogen sulfate were dissolved in 54 ml of 1 molar hydrochloric acid (0.054 mol) with cooling (T<5° C.). Whilst stirring vigorously and cooling, 1.24 g (0.018 mol) of sodium nitrite were then added, the temperature not exceeding 5° C. Towards the end of the addition of the nitrite, testing for free nitrous acid was carried out using iodine starch paper. Nitrous acid was added for as long as the test still gave a positive result 5 minutes after the addition. Excess nitrous acid was destroyed with a small amount of urea.

A hydrochloric acid solution (10 ml of 1M hydrochloric acid) containing 5.00 g (0.0044 mol) of β-cyclodextrin was added to the resulting solution and refluxed for 5 hours. The solution was neutralised with sodium carbonate and the product was salted out using finely ground sodium chloride. The product was filtered off and recrystallised from a small amount of water. A pale yellow crystalline powder (4) was obtained.

Example 7

5 g of cotton were immersed in a solution of 10 g of 4 from Example 6 in 100 ml of demineralised water. The pH of the solution was adjusted to 10.0 using 1.0 mol/l NaOH solution. After being completely wetted, the fabric was padded (liquor take-up 80%), dried in a Matthis dryer at 80° C. for 10 minutes and fixed at 160° C. for 7 minutes. The fabric was then thoroughly rinsed once using hot water and three times using cold water. Detection of the covalently bonded cyclodextrins on the cotton was carried out by measuring the colour discharged from an alkaline phenolphthalein solution.

We claim:

1. A process for the preparation of reactive cyclodextrins, in which process the cyclodextrins CD are reacted with a bifunctional compound X-spacer-Y,
   wherein X is a group which reacts with CD,
   the spacer is an aliphatic, cycloaliphatic or aromatic hydrocarbon radical containing from 1 to 25 carbon atoms,
   Y is a functional group which is reacted with a Z-Reactive or is a Reactive which Reactive is capable of reaction with cellulosic or proteinic materials,
   X is halogen,
   Z is acid halide or diazonium, and
   the Reactive or the Reactive of Z-Reactive is 2,3-dibromopropionyl, 2-bromoacryloxyl, 2-chloroacryloyl, methacryloyl, acryloxyl group, a vinyl sulfone group, a halotriazinyl or haloquinoxazolinoyl group, or a phenyl sulfonyl ethyl hydrogen sulphate radical or a phenyl sulfonyl ethyl sulfonic acid radical,
   when Y is a functional group which is reacted with the Reactive, the functional group is an amine or a phenyl,
   and the cyclodextrins CD is defined as an α, β or γ cyclodextrin derivative selected from substituted or unsubstituted cyclodextrins or mixtures thereof and the term substituted cyclodextrin derivative means that the cyclodextrin may be substituted one or more times by $C_{1-14}$alkyl, $C_{2-14}$alkenyl, OH, carbonyl, carboxyl or amine groups.

2. A process according to claim 1, wherein the spacer is —$(CH_2)_n$— and n is an integer from 1 to 8.

3. A process according to claim 2, wherein n is an integer from 2 to 6.

4. A process according to claim 1, wherein the functional groups of the bifunctional compound are arranged in terminal positions.

5. A process according to claim 1, wherein X is halogen, Y is an amino group, the bifunctional compound being in the form of a salt, Z is an acid halide group the spacer is —$(CH_2)_n$— and n is an integer from 1 to 8.

6. A process according to claim 5, wherein X is chlorine or bromine and n is 2 or 3.

7. A process according to claim 5, wherein the Z-Reactive is an acid halide of 2-bromoacrylic acid, 2-chloroacrylic acid, methacrylic acid, acrylic acid, 2,3-dibromopropionic acid, 2,3-dichlorodimoxalic acid.

8. A process according to claim 1, wherein X is halogen and Y is a phenyl group.

9. A process according to claim 8, wherein the Z is a diazonium function.

10. A process according to claim 9, wherein the Z-Reactive is diazonium phenyl sulfonyl ethyl hydrogen sulphate radical or a diazonium phenyl sulfonyl ethyl sulfonic acid radical.

11. A process according to claim 1, wherein the cyclodextrins are reacted in one step with a compound X-spacer-Reactive as defined in claim 1.

12. A process according to claim 1, wherein the Reactive is cyanuric chloride.

13. A process for the preparation of reactive cyclodextrins, in which process the cyclodextrins CD are reacted with a bifunctional compound X-spacer-Y, wherein X is a group which reacts with CD, the spacer is an aliphatic, cycloaliphatic or aromatic hydrocarbon radical containing from 1 to 25 carbon atoms and Y is a functional group which is reacted with a Reactive or Y is the Reactive
   which is capable of reaction with cellulosic or proteinic materials,
   wherein the X is halogen, and
   the Reactive is 2,3-dibromopropionyl, 2-bromoacryloxyl, 2- chloroacryloyl, methacryloyl, acryloxyl group, vinyl sulfone group, or phenyl sulfonyl ethyl hydrogen sulphate radical or a phenyl sulfonyl ethyl sulfonic acid radical and
   when Y is a functional group which is reacted with the Reactive, the functional group is an amine or a phenyl,
   and the cyclodextrins CD is defined as an a, 13 or ? cyclodextrin derivative selected from substituted or unsubstituted cyclodextrins or mixtures thereof and the term substituted cyclodextrin derivative means that the cyclodextrin may be substituted one or more times by $C_{1-14}$alkyl, $C_{2-14}$alkenyl, OH, carbonyl, carboxyl or amine groups.

* * * * *